(12) United States Patent
Urakawa et al.

(10) Patent No.: US 11,464,392 B2
(45) Date of Patent: Oct. 11, 2022

(54) OPTICAL MODULE AND ENDOSCOPE

(71) Applicant: OLYMPUS CORPORATION, Tokyo (JP)

(72) Inventors: Tsutomu Urakawa, Hachioji (JP); Susumu Kawata, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 273 days.

(21) Appl. No.: 16/808,494

(22) Filed: Mar. 4, 2020

(65) Prior Publication Data
US 2020/0196832 A1 Jun. 25, 2020

Related U.S. Application Data

(63) Continuation of application No. PCT/JP2018/018477, filed on May 14, 2018.

(30) Foreign Application Priority Data

Sep. 25, 2017 (JP) .............................. JP2017-183397

(51) Int. Cl.
*A61B 1/00* (2006.01)
*G02B 23/24* (2006.01)
*G02B 6/42* (2006.01)

(52) U.S. Cl.
CPC ...... *A61B 1/00004* (2013.01); *A61B 1/00013* (2013.01); *A61B 1/00126* (2013.01);
(Continued)

(58) Field of Classification Search
CPC ............ A61B 1/00004; A61B 1/00126; A61B 1/00013; A61B 1/051; G02B 23/2461;
(Continued)

(56) References Cited

U.S. PATENT DOCUMENTS 5,919,383 A 7/1999 Beguin et al.
6,019,523 A * 2/2000 Honmou ............. H01L 31/0203
257/E31.118
(Continued)

FOREIGN PATENT DOCUMENTS

EP 3199093 A1 8/2017
JP H07-51223 A 2/1995
(Continued)

OTHER PUBLICATIONS

International Search Report dated Jul. 31, 2018 issued in PCT/JP2018/018477.

*Primary Examiner* — Michael J Carey
*Assistant Examiner* — Christen A. Sharpless
(74) *Attorney, Agent, or Firm* — Scully, Scott, Murphy & Presser, P.C.

(57) ABSTRACT

An optical module is configured being provided with: a first case fixed to an implementation surface of an implementation substrate to cover an LD and an LD driver; a first filler filled in the first case to seal the LD and the LD driver; a second case fixed to the implementation surface of the implementation substrate to cover the first case in a state of not adhering to the first case; a third case accommodating the implementation substrate and the second case inside; and a second filler filled in the third case to seal the implementation substrate and the second case.

7 Claims, 6 Drawing Sheets

(52) U.S. Cl.
CPC ......... *G02B 6/4212* (2013.01); *G02B 6/4214* (2013.01); *G02B 23/2461* (2013.01); *G02B 23/2476* (2013.01)

(58) Field of Classification Search
CPC ................ G02B 23/2476; G02B 23/26; G02B 23/2484; G02B 6/42; G02B 6/4212; H04N 5/2257; H04N 2005/2255; H01S 5/022
USPC ........................................................ 600/103
See application file for complete search history.

(56) References Cited

U.S. PATENT DOCUMENTS

| | | | |
|---|---|---|---|
| 6,080,101 A | 6/2000 | Tatsuno et al. | |
| 2003/0095346 A1 | 5/2003 | Nasu et al. | |
| 2012/0245420 A1* | 9/2012 | Yoshida | A61B 1/00165 600/178 |
| 2015/0087092 A1* | 3/2015 | Goto | H01L 33/005 438/27 |
| 2016/0109669 A1 | 4/2016 | Moidu | |
| 2016/0211919 A1 | 7/2016 | Urakawa et al. | |
| 2016/0262599 A1* | 9/2016 | Nakagawa | A61B 1/0057 |

FOREIGN PATENT DOCUMENTS

| | | | | |
|---|---|---|---|---|
| JP | 2002-516596 A | | 6/2002 | |
| JP | 2002-299648 A | | 10/2002 | |
| JP | 2002299648 A | * | 10/2002 | |
| JP | 2003-021734 A | | 1/2003 | |
| JP | 2003021734 A | * | 1/2003 | |
| JP | 2003-142767 A | | 5/2003 | |
| JP | 2003142767 A | * | 5/2003 | ........... G02B 6/4257 |
| JP | 5851661 B1 | | 2/2016 | |
| WO | WO 98/24695 A2 | | 6/1998 | |
| WO | WO 2016/047172 A1 | | 3/2016 | |

* cited by examiner

OPTICAL MODULE AND ENDOSCOPE

CROSS REFERENCE TO RELATED APPLICATION

This application is a continuation application of PCT/JP2018/018477 filed on May 14, 2018 and claims benefit of Japanese Application No. 2017-183397 filed in Japan on Sep. 25, 2017, the entire contents of which are incorporated herein by this reference.

BACKGROUND OF INVENTION

1. Field of the Invention

The present invention relates to an optical module that converts an electrical signal to an optical signal to transmit the optical signal, and an endoscope.

2. Description of the Related Art

Conventionally, among endoscopes, electronic endoscopes provided with an image sensor such as a CMOS on a distal end portion of an elongated insertion portion have been widely adopted. Recently, in this kind of endoscope, increase in the number of pixels of the image sensor has been advanced.

When the number of pixels of the image sensor is increased, however, a signal volume transmitted from the image sensor to a signal processing apparatus (a processor) increases. In this case, it is preferable that transmission of an image pickup signal acquired by the image sensor is performed by transmission of an optical signal via a thin optical fiber instead of transmission of an electrical signal via metal wiring.

In general, for an optical module for performing such optical signal transmission, a structure is adopted in which a light emitting device, such as a laser diode, configured to convert an electrical signal to an optical signal, and an electronic part configured to drive the light emitting device are implemented on a substrate, and one end side of an optical fiber is optically connected to the light emitting device on the substrate.

Furthermore, in an optical module, a structure is widely adopted in which the substrate on which the light emitting device and the electronic part are implemented is sealed with a filler or the like for the purpose of waterproofness and the like. For example, Japanese Patent Application Laid-Open Publication No. 2002-299648 discloses a technique for protecting each device and a substrate from water and gases by placing an optical transmission module (an optical module) in a mold, completely sealing the optical transmission module by pouring resin mixture into the mold and causing the resin mixture to solidify, and, furthermore, covering an exterior with a metal casing.

SUMMARY OF THE INVENTION

An optical module according to an aspect of the present invention is provided with: a light emitting device; an electronic part configured to drive the light emitting device; a substrate with the light emitting device and the electronic part implemented on one surface of the substrate; a first case fixed to the one surface of the substrate to cover the light emitting device and the electronic part; a first filler filled in the first case to seal the light emitting device and the electronic part; a second case fixed to the one surface of the substrate to cover the first case in a state of not adhering to the first case; a third case accommodating the substrate and the second case inside; and a second filler filled in the third case to seal the substrate and the second case.

An endoscope according to an aspect of the present invention is provided with an image sensor and the above optical module on a distal end portion of an insertion portion, wherein the optical module converts an image pickup signal from the image sensor to an optical signal.

DETAILED DESCRIPTION OF THE PREFERRED EMBODIMENT

Figure 1:
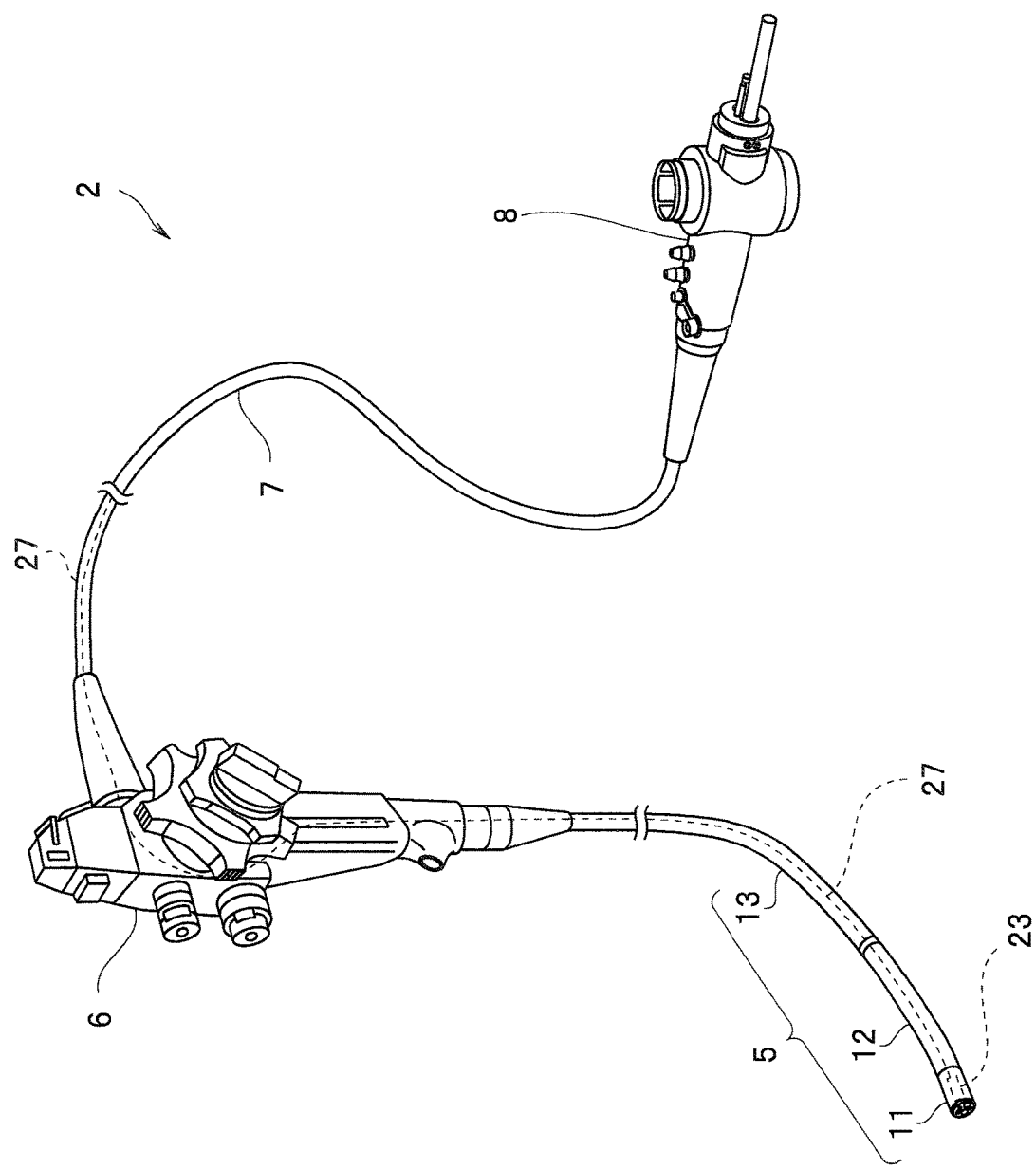
FIG. 1 is a perspective view of an endoscope.
Figure 2:
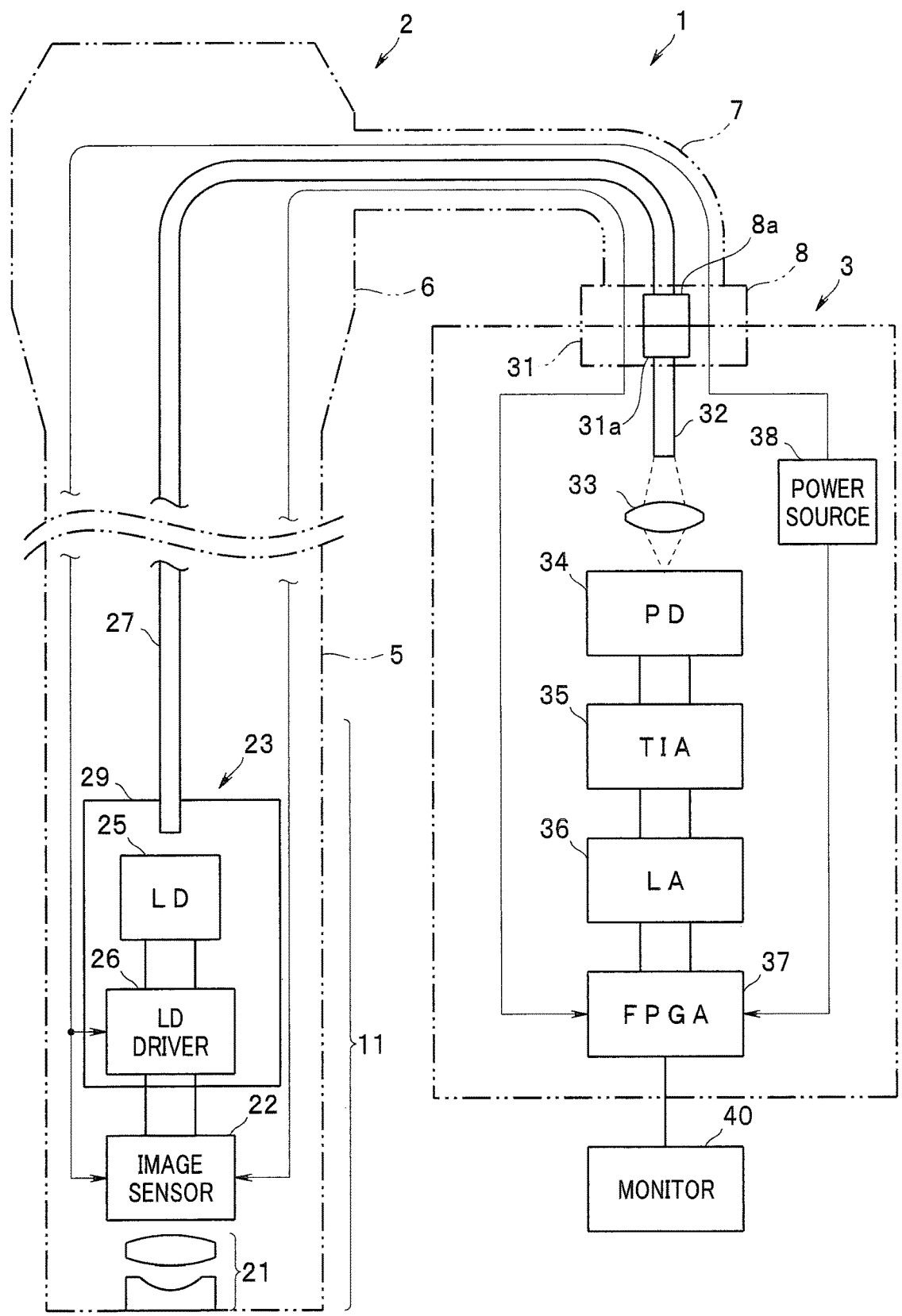
FIG. 2 is a functional block diagram showing a video signal transmission system in an endoscope system.
Figure 3:
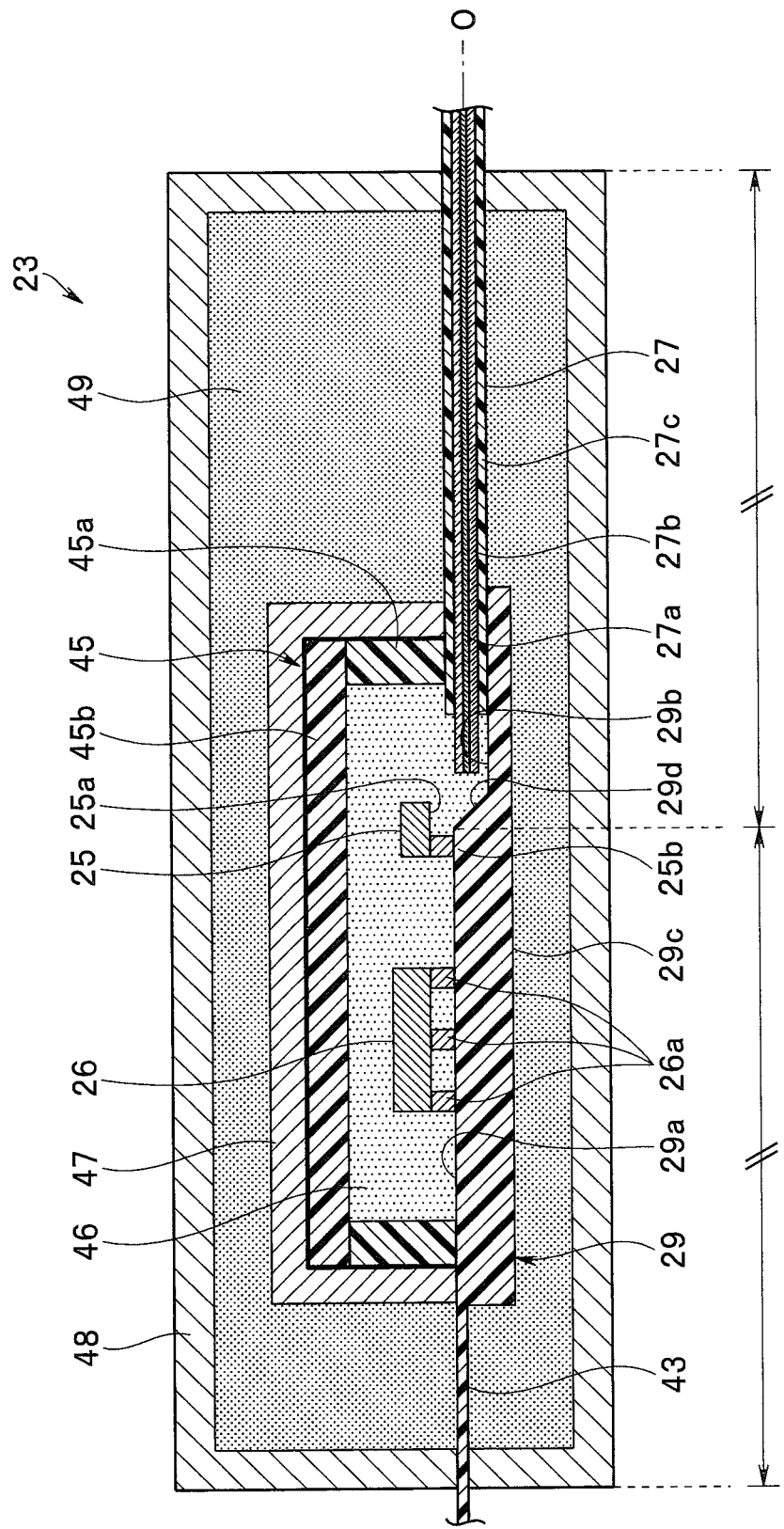
FIG. 3 is a sectional view schematically showing an optical module.
Figure 4:
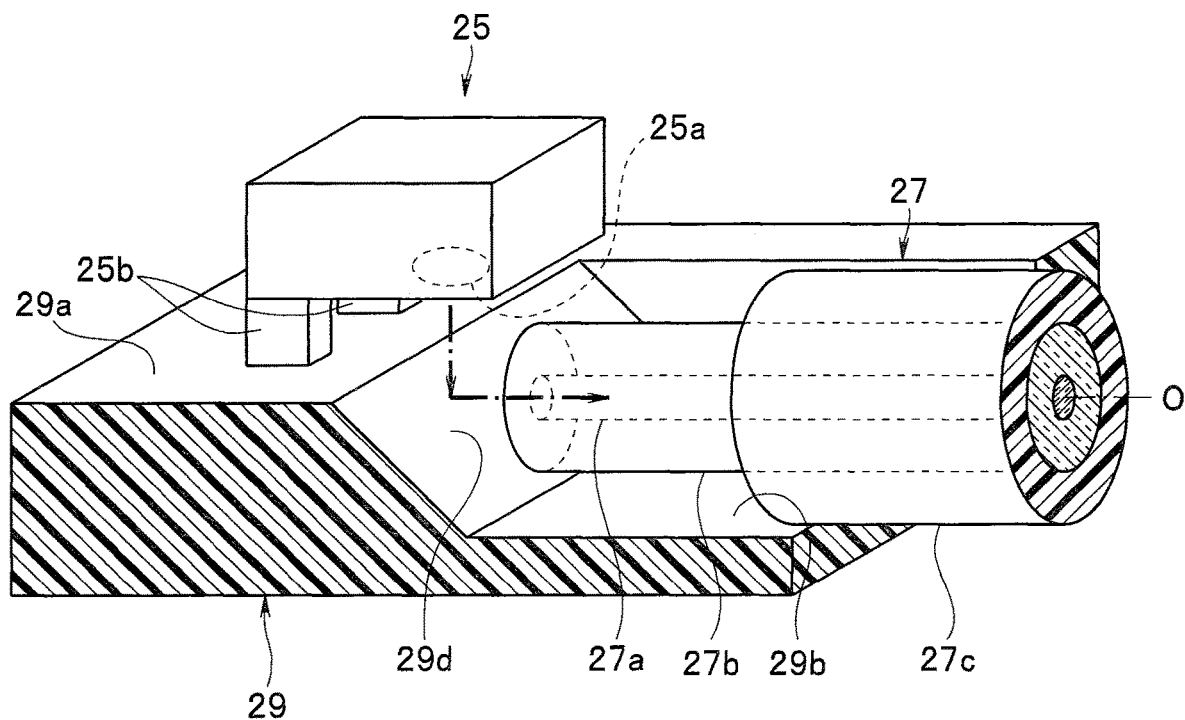
FIG. 4 is a perspective view schematically showing a relationship between a light emitting device and an optical fiber.

An embodiment of the present invention will be described below with reference to drawings. The drawings relate to the embodiment of the present invention. FIG. 1 is a perspective view of an endoscope; FIG. 2 is a functional block diagram showing a video signal transmission system in an endoscope system; FIG. 3 is a sectional view schematically showing an optical module; and FIG. 4 is a perspective view schematically showing a relationship between a light emitting device and an optical fiber.

An endoscope 2 shown in FIG. 1 is configured having an elongated insertion portion 5, an operation portion 6 disposed on a proximal end side of the insertion portion 5, a universal cord 7 extended from the operation portion 6, and a connector 8 disposed on a proximal end side of the universal cord 7. Note that if the endoscope 2 of the present embodiment is a surgical endoscope, cleaning/sterilization treatment for the endoscope 2 is performed under a high-temperature, high-pressure and high-humidity environment by autoclave sterilization or the like.

The insertion portion 5 is configured with a rigid distal end portion 11, a bending portion 12 for causing a direction of the distal end portion 11 to change, and an elongated flexible portion 13 connectedly provided in that order from a distal end side.

As shown in FIG. 2, in the distal end portion 11, an image pickup optical unit 21, an image sensor 22 configured to pick up an optical image formed by the image pickup optical unit 21, and an optical module 23 which is an E/O module configured to convert an image pickup signal (an electrical signal) from the image sensor 22 to an optical signal are disposed.

The image sensor 22 is configured with a solid-state image pickup device such as a CMOS (complementary metal oxide semiconductor) or a CCD (charge coupled device).

The optical module 23 is configured being provided with a laser diode (LD) 25 as a light emitting device, an LD driver 26 as an electronic part configured to perform driving control of the LD 25 based on an image pickup signal from the image sensor 22 to cause the LD 25 to emit an optical signal, an optical fiber 27, one end side of which is optically connected to the LD 25, and an implementation substrate 29 as a substrate on which the LD 25 and the LD driver 26 are implemented and which holds one end portion of the optical fiber 27.

Here, the optical fiber 27 is configured, for example, with a multi-mode fiber. The other end side of the optical fiber 27 passes through the operation portion 6 and is inserted in the universal cord 7, and can be connected to a processor 3 via a plug 8a of an optical connector provided on the connector 8.

As shown in FIG. 2, the processor 3 is for constituting an endoscope system 1 together with the endoscope 2 and has a connector 31 which the connector 8 of the endoscope 2 is attachable to and detachable from, and an optical fiber 32 optically connected to the optical fiber 27 (the plug 8a) via a receptacle 31a of an optical connector provided on the connector 31.

The processor 3 also has a lens 33 for condensing an optical signal transmitted from the optical fiber 27 to the optical fiber 32, a photodiode (PD) 34 configured to photoelectrically converts the optical signal condensed by the lens 33, a transimpedance amplifier (TIA) 35 configured to impedance-convert and amplify a current signal photoelectrically converted by the PD 34 to output the current signal as a voltage signal, and a limiting amplifier (LA) 36 configured to cause an amplitude of the voltage signal outputted from the TIA 35 to be increased and constant.

The processor 3 also has a field programmable gate array (FPGA) 37 as an image pickup controlling portion configured to output a clock signal and a control signal to the image sensor 22 and the like via a signal line and process the voltage signal from the LA 36 to display an object image on a monitor 40.

Note that the processor 3 includes a power source circuit 38 within, and the power source circuit 38 is capable of supplying drive power and the like to each portion of the endoscope 2 and the processor 3 via electrical wiring.

Next, a detailed structure of the optical module 23 will be described with reference to FIGS. 3 and 4.

As shown in FIGS. 3 and 4, in the optical module 23 of the present embodiment, a surface emitting type semiconductor laser with a smaller drive current and a smaller heating value than those of an edge emitting laser is adopted in consideration of the LD 25 being arranged on the distal end portion 11 of the endoscope 2.

More specifically, the LD 25 is configured, for example, with a so-called flip-chip type vertical cavity surface emitting laser (VCSEL) provided with anode and cathode bumps 25b on a surface on the same side as a light emitting surface 25a.

The LD driver 26 is configured, for example, with a so-called flip-chip type IC circuit, which is provided with a plurality of bumps 26a on a surface facing the implementation substrate 29.

The optical fiber 27 is configured being provided with a core 27a located at a central part, a clad 27b covering an outer circumference of the core 27a and an outer cover 27c covering an outer circumference of the clad 27b.

At one end portion of the optical fiber 27, the core 27a and the clad 27b project from the outer cover 27c.

The implementation substrate 29 is configured with a flat plate-shaped substrate, one surface of which is set as an implementation surface 29a. For example, one end side of the implementation substrate 29 is integrally formed on the other end side of a flexible substrate 43 that is electrically connected to the image sensor 22. More specifically, the implementation substrate 29 of the present embodiment is configured by laminating reinforcement plates with a predetermined thickness on the other end portion of the flexible substrate 43. Note that it is also possible for the implementation substrate 29 and the flexible substrate 43 to be configured with separate bodies and electrically connected via terminal portions.

On the implementation surface 29a of the implementation substrate 29, a plurality of terminal portions (not shown) corresponding to the respective bumps 25b of the LD 25 and the respective bumps 26a of the LD driver 26 are provided. By the respective bumps 25b and 26a being electrically connected to the terminal portions, the LD 25 and the LD driver 26 are held (implemented) on the implementation substrate 29.

On the implementation surface 29a side of the implementation substrate 29, a holding groove 29b facing the light emitting surface 25a of the LD 25 is provided. In the holding groove 29b, one end portion of each of the core 27a and the clad 27b projecting from the outer cover 27c of the optical fiber 27 is held. The implementation surface 29a of the implementation substrate 29 and the holding groove 29b are connected via a sloped surface. The sloped surface is machined to be inclined at 45 degrees relative to an optical axis 0, and a mirror portion 29d is formed on the machined sloped surface by plating Au. Thereby, it becomes possible to cause light from the LD 25 to be reflected by the mirror portion 29d and optically coupled with the core 27a. In other words, by an end face of the held core 27a facing the light emitting surface 25a of the LD 25 at an angle of 90 degrees via the mirror portion 29d, the LD 25 and the optical fiber 27 are optically connected.

To the implementation surface 29a of the implementation substrate 29 where the LD 25 and the LD driver 26 are implemented, and the one end portion of the optical fiber 27 is held as described above, a first case 45 covering the LD 25, the LD driver 26 and the one end portion of the optical fiber 27 at a predetermined interval is fixed.

More specifically, the first case 45 of the present embodiment is configured, for example, having a resin frame body 45a surrounding the LD 25, the LD driver 26 and the one end portion of the optical fiber 27, and a resin lid body 45b fixed to an open end of the frame body 45a to close the frame body 45a. Here, of the component members of the first case 45, at least the lid body 45b is configured with material with a smaller thermal expansion stress than that of a first filler 46 described later. Note that the frame body 45a can be similarly configured with material with a smaller thermal expansion stress than that of the first filler 46.

Inside the first case 45, the first filler 46 is filled. The first filler 46 is filled into the frame body 45a, for example, after the frame body 45a is fixed to the implementation substrate 29, and before the lid body 45b is bonded to the frame body 45a. By the first filler 46 being filled as described above, the LD 25, the LD driver 26 and the one end portion of the optical fiber 27 arranged in the first case 45 are sealed.

Here, in order to maintain optical connection between the LD 25 and the optical fiber 27, an adhesive or the like with optically transparent material having a refractive index equivalent to a refractive index of the optical fiber 27 is adopted as the first filler 46. More specifically, for example, if quartz glass is used for the optical fiber 27, a transparent silicone-based adhesive with a refractive index (about 1.4) equivalent to a refractive index of quartz glass is favorably used as the first filler 46.

Further, to the implementation surface 29a of the implementation substrate 29, a second case 47 covering an exterior of the first case 45 is fixed. The second case 47 is, for example, a shield case configured with material such as metal and is in contact with an outer surface of the first case 45 in a state of not adhering to the outer surface (that is, the second case 47 is fixed to the implementation surface 29a in a state of being substantially closely adhering to the first case 45 with a slight air layer between the second case 47 and the first case 45).

The implementation substrate 29 to which the second case 47 is fixed as described above is accommodated inside a third case 48. The third case 48 is, for example, a shield case configured with material such as metal, and the implementation substrate 29 and the second case 47 are arranged such that a non-implementation surface 29c, which is the other surface of the implementation substrate 29, and an outer surface of the second case 47 are at a predetermined interval from an inner surface of the third case 48. Further, the implementation substrate 29 and the second case 47 are arranged such that the LD 25 is located substantially in a center of the third case 48.

Furthermore, inside the third case 48, a second filler 49 is filled. In other words, the second filler 49 is interposed between the non-implementation surface 29c of the implementation substrate 29 and the third case 48 and between the outer surface of the second case 47 and the third case 48. By the second filler 49 being filled as described above, the implementation substrate 29 and the second case 47 are sealed.

Here, an adhesive or the like with a lower moisture absorption rate and a lower water absorption rate than those of the first filler 46 is adopted as the second filler 49. More specifically, for example, an epoxy-based adhesive is favorably used as the second filler 49. Note that though a water absorption rate of the transparent silicone-based adhesive is about 5 to 10%, a water absorption rate of the epoxy-based adhesive is about 0.1 to 0.2%.

According to such an embodiment, by the first case 45 fixed to the implementation surface 29a of the implementation substrate 29 to cover the LD 25 and the LD driver 26, the first filler 46 filled in the first case 45 to seal the LD 25 and the LD driver 26, the second case 47 fixed to the implementation surface 29a of the implementation substrate 29 to cover the first case 45 in a state of not adhering to the first case 45, the third case 48 accommodating the implementation substrate 29 and the second case 47 inside, and the second filler 49 filled in the third case 48 to seal the implementation substrate 29 and the second case 47 being provided, it is possible to prevent detachment of the LD 25 and the LD driver 26 from the implementation substrate 29 under a high-temperature environment and prevent deterioration of the LD 25 under a high-humidity environment.

In other words, by fixing the first case 45 covering the LD 25 and the LD driver 26 to the implementation surface 29a of the implementation substrate 29, and filling the first filler 46 in the first case 45 to seal the LD 25 and the LD driver 26, it is possible to, even in the case of having to select material with a large thermal expansion stress for the first filler 46, suppress thermal expansion of the first filler 46 in a thickness direction of the implementation substrate 29 by the first case 45. Therefore, it is possible to suppress a thermal expansion stress of the first filler 46 pulling the implementation surface 29a in the thickness direction, and it is possible to, when sealing by the first filler 46 is performed, prevent detachment of the LD 25 and the LD driver 26 due to deflection and the like of the implementation substrate 29.

Further, by providing the second case 47 fixed to the implementation surface 29a of the implementation substrate 29 to cover the first case 45 in a state of not adhering to the first case 45, causing the implementation substrate 29 and the second case 47 to be accommodated inside the third case 48, and filling the second filler 49 in the third case 48 to seal the implementation substrate 29 and the second case 47, it is possible to, even in the case of having to select material with a high moisture absorption rate and a high water absorption rate for the first filler 46, secure moistureproofness and waterproofness for the LD 25 by selecting material with a low moisture absorption rate and a low water absorption rate for the second filler 49. In addition, by interposing the second case 47 covering the first case 45 in a state of not adhering to the first case 45 between the first case 45 filled with the first filler 46 and the second filler 49, it is possible to appropriately prevent a thermal expansion stress of the second filler 49 from being transmitted to the implementation surface 29a of the implementation substrate 29 via the first case 45 and the first filler 46. Therefore, when sealing by the second filler 49 is performed (when the first filler 46 and the second filler 49 are laminated on the implementation surface 29a side), it is possible to prevent detachment of the LD 25 and the LD driver 26 due to deflection and the like of the implementation substrate 29.

In this case, by configuring the lid body 45b of the first case 45 with rigid material with a smaller thermal expansion stress than that of the first filler 46, it is possible to properly suppress the thermal expansion of the first filler 46 in the thickness direction of the implementation substrate 29.

Further, by causing the second filler 49 to be interposed not only between the outer surface of the second case 47 and the third case 48 but also between the non-implementation surface 29c of the implementation substrate 29 and the third case 48, it is possible to offset the thermal expansion stress transmitted from the first filler 46 to the implementation surface 29a by the thermal expansion stress transmitted from the second filler 49 to the non-implementation surface 29c. Thereby, it is possible to more properly suppress deflection of the implementation substrate 29 and suppress detachment of the LD 25 and the LD driver 26.

Further, by causing the LD 25 to be located substantially in the center of the third case 48, it is possible to improve moistureproofness and waterproofness by the first and second fillers 46 and 49 more and prevent deterioration of the LD 25 more properly.

Figure 5:
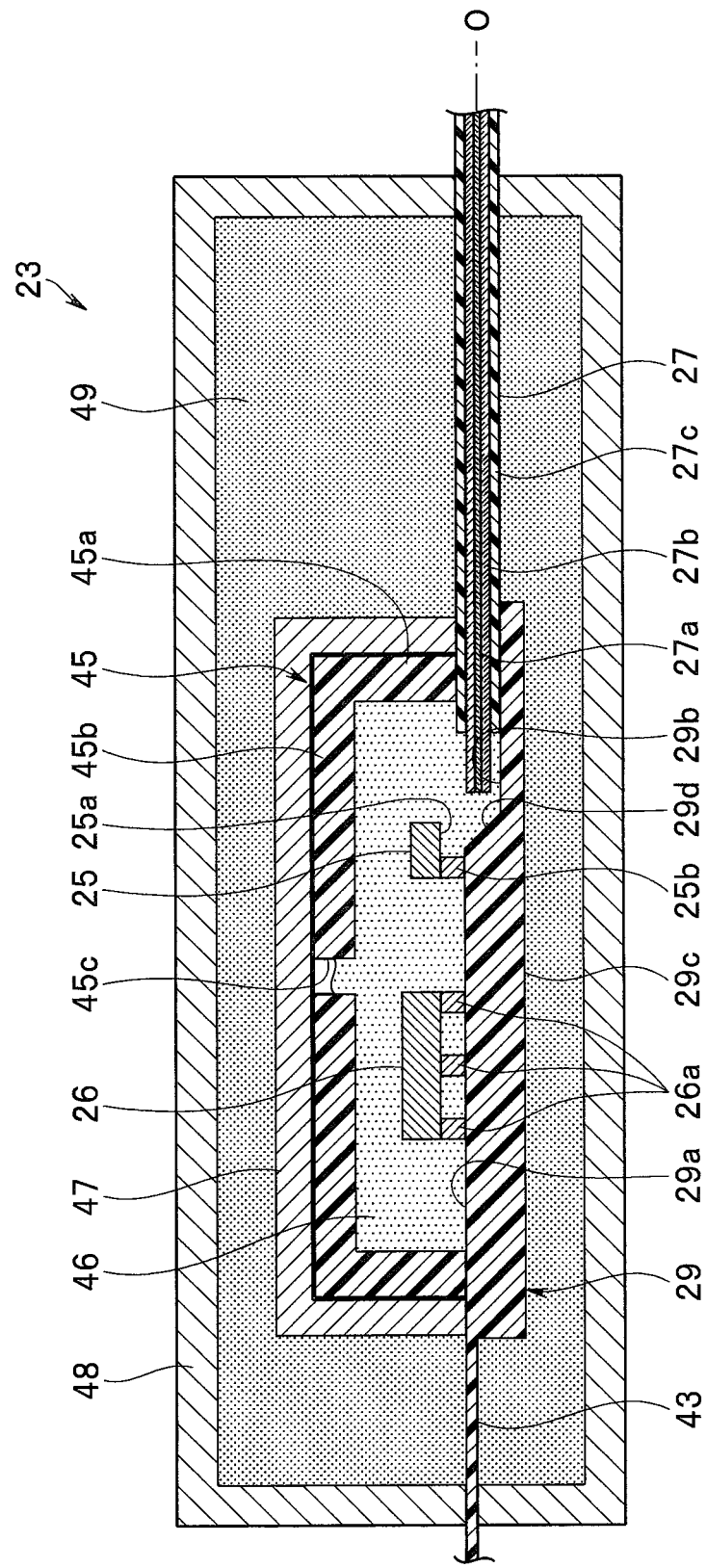
FIG. 5 is a sectional view schematically showing the optical module according to a first modification.

Here, for example, as shown in FIG. 5, the first case 45 may be such that the frame body 45a and the lid body 45b are integrally formed. In this case, for example, by injecting the first filler 46 via an injection hole 45c formed in the lid body 45b, sealing of the LD 25 and the like by the first filler 46 is possible.

Figure 6:
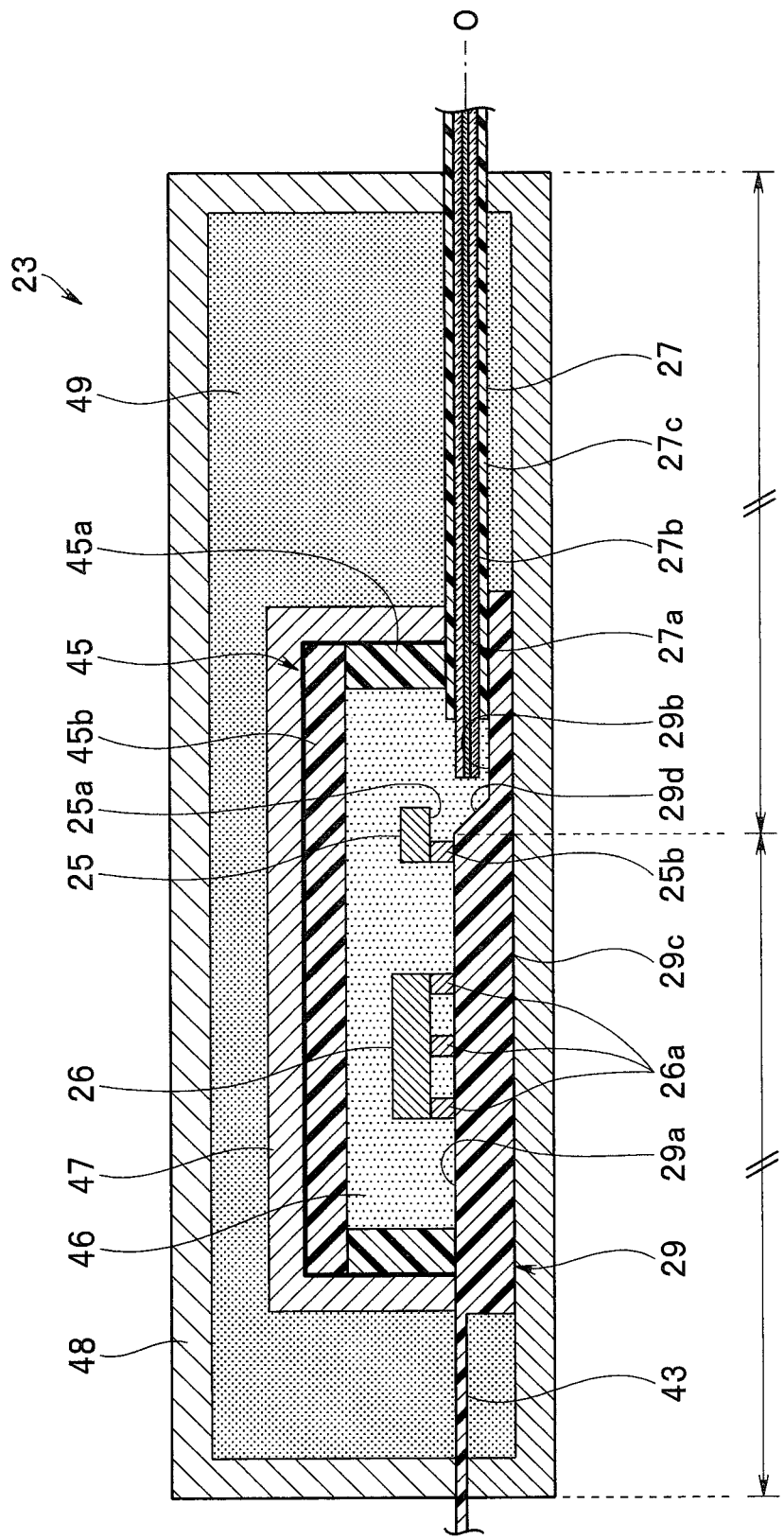
FIG. 6 is a sectional view schematically showing the optical module according to a second modification.

Further, for example, as shown in FIG. 6, if the thermal expansion stresses transmitted from the first filler 46 and the second filler 49 to the implementation surface 29a are small, it is possible to cause the non-implementation surface 29c of the implementation substrate 29 to be in contact with the third case 48 and omit interposition of the second filler 49 between the non-implementation surface 29c and the third case 48.

Note that the present invention is not limited to the embodiment described above, but various modifications and changes are possible. The modifications and changes are also within the technical scope of the present invention.

For example, though an example of a configuration in which the optical module 23 is arranged on the distal end portion 11 of the endoscope 2 has been described in the above embodiment, the present invention is not limited to the configuration. For example, the optical module 23 can be arranged on the operation portion 6 of the endoscope 2. Furthermore, it is, of course, possible to apply the optical module 23 to equipment other than an endoscope.

What is claimed is:

1. An optical module comprising:
a light emitting device;
an electronic part configured to drive the light emitting device;
a substrate with the light emitting device and the electronic part implemented on one surface of the substrate;
a first case fixed to the one surface of the substrate to cover the light emitting device and the electronic part;
a first filler filled in the first case to seal the light emitting device and the electronic part;
a second case fixed to the one surface of the substrate to cover the first case in a state of not adhering to the first case;
a third case accommodating the substrate and the second case inside;
a second filler filled in the third case to seal the substrate and the second case; and
an optical fiber having one end side held by the one surface of the substrate;
wherein a mirror is formed on the one surface, the mirror being configured to reflect an optical signal emitted from the light emitting device, to cause the optical signal to be incident on one end of the optical fiber via the first filler; and
the first filler comprises an optically transparent material having a refractive index equivalent to a refractive index of the optical fiber.

2. The optical module according to claim 1, wherein the first case is fixed to the one surface of the substrate and includes a frame body surrounding the light emitting device and the electronic part and a lid body closing an open end of the frame body.

3. The optical module according to claim 2, wherein the lid body is configured with a material having a smaller thermal expansion stress than that of the first filler.

4. The optical module according to claim 1, wherein the second filler is configured with a material having a lower moisture absorption rate and a lower water absorption rate than those of the first filler.

5. The optical module according to claim 1, wherein the second filler is interposed between another surface of the substrate and the third case and between an outer surface of the second case and the third case.

6. The optical module according to claim 1, wherein the light emitting device is located substantially in a center of the third case.

7. An endoscope comprising an image sensor and the optical module according to claim h on a distal end portion of an insertion portion, wherein
the optical module converts an image pickup signal from the image sensor to an optical signal.

* * * * *